(12) United States Patent
Cahill

(10) Patent No.: US 9,138,562 B2
(45) Date of Patent: Sep. 22, 2015

(54) FLEXIBLE CATHETER SYSTEM

(75) Inventor: Ryan Cahill, Newtonville, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 955 days.

(21) Appl. No.: 12/105,397

(22) Filed: Apr. 18, 2008

(65) Prior Publication Data

US 2008/0262422 A1     Oct. 23, 2008

Related U.S. Application Data

(60) Provisional application No. 60/923,985, filed on Apr. 18, 2007.

(51) Int. Cl.
| | | |
|---|---|---|
| A61M 25/01 | (2006.01) | |
| A61M 25/06 | (2006.01) | |
| A61M 25/00 | (2006.01) | |

(52) U.S. Cl.
CPC ....... *A61M 25/0147* (2013.01); *A61M 25/0138* (2013.01); *A61M 25/0662* (2013.01); *A61M 25/0071* (2013.01); *A61M 2025/015* (2013.01)

(58) Field of Classification Search
CPC .................. A61M 2025/015; A61M 25/0071; A61M 25/0138; A61M 25/0147; A61M 25/0662
USPC .......... 604/95.04, 533–535; 138/20; 219/550; 600/585
See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |

(Continued)

FOREIGN PATENT DOCUMENTS

| | | |
|---|---|---|
| DE | 9413645 U1 | 10/1994 |
| EP | 0362113 | 4/1990 |

(Continued)

OTHER PUBLICATIONS

Athanasiou, T., "Coronary Artery Bypass with the Use of a Magnetic Distal Anastomotic Device: Surgical Technique and Preliminary Experience," The Heart Surgery Forum #2004-1024, 2004, 4 pgs.

(Continued)

*Primary Examiner* — Imani Hayman
(74) *Attorney, Agent, or Firm* — DLA Piper LLP (US)

(57) ABSTRACT

A percutaneous delivery system with a high degree of flexibility is provided. In one embodiment, the system includes a catheter having a portion comprising multiple segments, linked in series by at least one connecting wire. Joints between the multiple segments provide a high degree of flexibility. In some embodiments, only a distal portion is made up of segments. In other embodiments, the whole length of the catheter is made up of segments. Manipulation of the at least one connecting wire enables manipulation of the segments to flex a portion of the catheter. In one aspect, the invention provides a delivery system that reduces the impact of the delivery system on the final release position of the implant delivered. The delivery system can be used to deploy and/or retrieve implantable medical devices, for example, patent foramen ovale (PFO) occluder.

14 Claims, 3 Drawing Sheets

(56) References Cited

U.S. PATENT DOCUMENTS

| | | | |
|---|---|---|---|
| 4,626,245 | A | 12/1986 | Weinstein |
| 4,693,249 | A | 9/1987 | Schenck et al. |
| 4,696,300 | A | 9/1987 | Anderson |
| 4,710,181 | A | 12/1987 | Fuqua |
| 4,710,192 | A | 12/1987 | Liotta et al. |
| 4,738,666 | A | 4/1988 | Fuqua |
| 4,836,204 | A | 6/1989 | Landymore et al. |
| 4,840,623 | A | 6/1989 | Quackenbush |
| 4,902,508 | A | 2/1990 | Badylak et al. |
| 4,915,107 | A | 4/1990 | Rebuffat et al. |
| 4,917,089 | A | 4/1990 | Sideris |
| 4,921,479 | A | 5/1990 | Grayzel |
| 4,956,178 | A | 9/1990 | Badylak et al. |
| 5,021,059 | A | 6/1991 | Kensey et al. |
| 5,037,433 | A | 8/1991 | Wilk et al. |
| 5,041,129 | A | 8/1991 | Hayhurst et al. |
| 5,049,131 | A | 9/1991 | Deuss |
| 5,078,736 | A | 1/1992 | Behl |
| 5,106,913 | A | 4/1992 | Yamaguchi et al. |
| 5,108,420 | A | 4/1992 | Marks |
| 5,149,327 | A | 9/1992 | Oshiyama et al. |
| 5,163,131 | A | 11/1992 | Row et al. |
| 5,167,363 | A | 12/1992 | Adkinson et al. |
| 5,167,637 | A | 12/1992 | Okada et al. |
| 5,171,259 | A | 12/1992 | Inoue et al. |
| 5,176,659 | A | 1/1993 | Mancini |
| 5,192,301 | A | 3/1993 | Kamiya et al. |
| 5,222,974 | A | 6/1993 | Kensey et al. |
| 5,226,879 | A | 7/1993 | Ensminger et al. |
| 5,236,440 | A | 8/1993 | Hlavacek |
| 5,245,023 | A | 9/1993 | Peoples et al. |
| 5,245,080 | A | 9/1993 | Aubard et al. |
| 5,250,430 | A | 10/1993 | Peoples et al. |
| 5,257,637 | A | 11/1993 | El Gazayerli |
| 5,275,826 | A | 1/1994 | Badylak et al. |
| 5,282,827 | A | 2/1994 | Kensey et al. |
| 5,284,488 | A | 2/1994 | Sideris |
| 5,304,184 | A | 4/1994 | Hathaway et al. |
| 5,312,341 | A | 5/1994 | Turi |
| 5,312,435 | A | 5/1994 | Nash et al. |
| 5,316,262 | A | 5/1994 | Koebler |
| 5,320,611 | A | 6/1994 | Bonutti et al. |
| 5,334,217 | A | 8/1994 | Das |
| 5,350,363 | A | 9/1994 | Goode et al. |
| 5,354,308 | A | 10/1994 | Simon et al. |
| 5,364,356 | A | 11/1994 | Hofling |
| 5,411,481 | A | 5/1995 | Allen et al. |
| 5,413,584 | A | 5/1995 | Schulze et al. |
| 5,417,699 | A | 5/1995 | Klein et al. |
| 5,425,744 | A | 6/1995 | Fagan et al. |
| 5,433,727 | A | 7/1995 | Sideris |
| 5,451,235 | A | 9/1995 | Lock et al. |
| 5,453,099 | A | 9/1995 | Lee et al. |
| 5,478,353 | A | 12/1995 | Yoon |
| 5,480,353 | A | 1/1996 | Garza, Jr. |
| 5,480,424 | A | 1/1996 | Cox |
| 5,486,193 | A | 1/1996 | Bourne et al. |
| 5,507,811 | A | 4/1996 | Koike et al. |
| 5,522,788 | A | 6/1996 | Kuzmak |
| 5,534,432 | A | 7/1996 | Peoples et al. |
| 5,540,712 | A | 7/1996 | Kleshinski et al. |
| 5,562,632 | A | 10/1996 | Davila et al. |
| 5,577,299 | A | 11/1996 | Thompson et al. |
| 5,601,571 | A | 2/1997 | Moss |
| 5,603,703 | A | 2/1997 | Elsberry et al. |
| 5,618,311 | A | 4/1997 | Gryskiewicz |
| 5,620,461 | A | 4/1997 | Muijs Van De Moer et al. |
| 5,626,599 | A | 5/1997 | Bourne et al. |
| 5,634,936 | A | 6/1997 | Linden et al. |
| 5,649,950 | A | 7/1997 | Bourne et al. |
| 5,649,959 | A | 7/1997 | Hannam et al. |
| 5,663,063 | A | 9/1997 | Peoples et al. |
| 5,683,411 | A | 11/1997 | Kavteladze et al. |
| 5,690,674 | A | 11/1997 | Diaz |
| 5,693,085 | A | 12/1997 | Buirge et al. |
| 5,702,421 | A | 12/1997 | Schneidt et al. |
| 5,709,707 | A | 1/1998 | Lock et al. |
| 5,713,864 | A | 2/1998 | Verkaart |
| 5,717,259 | A | 2/1998 | Schexnayder |
| 5,720,754 | A | 2/1998 | Middleman et al. |
| 5,725,552 | A | 3/1998 | Kotula et al. |
| 5,733,294 | A | 3/1998 | Forber et al. |
| 5,733,337 | A | 3/1998 | Carr, Jr. et al. |
| 5,741,297 | A | 4/1998 | Simon |
| 5,772,641 | A | 6/1998 | Wilson |
| 5,776,162 | A | 7/1998 | Kleshinski |
| 5,776,183 | A | 7/1998 | Kanesaka et al. |
| 5,797,960 | A | 8/1998 | Stevens et al. |
| 5,800,516 | A | 9/1998 | Fine et al. |
| 5,810,884 | A | 9/1998 | Kim |
| 5,820,594 | A | 10/1998 | Fontirroche et al. |
| 5,823,956 | A | 10/1998 | Roth et al. |
| 5,829,447 | A | 11/1998 | Stevens et al. |
| 5,853,420 | A | 12/1998 | Chevillon et al. |
| 5,853,422 | A | 12/1998 | Huebsch et al. |
| 5,855,614 | A | 1/1999 | Stevens et al. |
| 5,861,003 | A | 1/1999 | Latson et al. |
| 5,865,791 | A | 2/1999 | Whayne et al. |
| 5,879,366 | A | 3/1999 | Shaw et al. |
| 5,893,856 | A | 4/1999 | Jacob et al. |
| 5,902,287 | A | 5/1999 | Martin |
| 5,902,319 | A | 5/1999 | Daley |
| 5,904,703 | A | 5/1999 | Gilson |
| 5,919,200 | A | 7/1999 | Stambaugh et al. |
| 5,924,424 | A | 7/1999 | Stevens et al. |
| 5,928,250 | A | 7/1999 | Koike et al. |
| 5,944,691 | A | 8/1999 | Querns et al. |
| 5,944,738 | A | 8/1999 | Amplatz et al. |
| 5,955,110 | A | 9/1999 | Patel et al. |
| 5,976,174 | A | 11/1999 | Ruiz |
| 5,980,505 | A | 11/1999 | Wilson |
| 5,989,268 | A | 11/1999 | Pugsley, Jr. et al. |
| 5,993,475 | A | 11/1999 | Lin et al. |
| 5,993,844 | A | 11/1999 | Abraham et al. |
| 5,997,575 | A | 12/1999 | Whitson et al. |
| 6,010,517 | A | 1/2000 | Baccaro |
| 6,019,753 | A | 2/2000 | Pagan |
| 6,024,756 | A | 2/2000 | Huebsch et al. |
| 6,027,509 | A | 2/2000 | Schatz et al. |
| 6,027,519 | A | 2/2000 | Stanford |
| 6,030,007 | A | 2/2000 | Bassily et al. |
| 6,056,760 | A | 5/2000 | Koike et al. |
| 6,071,998 | A | 6/2000 | Muller et al. |
| 6,077,291 | A | 6/2000 | Das |
| 6,077,880 | A | 6/2000 | Castillo et al. |
| 6,079,414 | A | 6/2000 | Roth |
| 6,080,182 | A | 6/2000 | Shaw et al. |
| 6,096,347 | A | 8/2000 | Geddes et al. |
| 6,106,913 | A | 8/2000 | Scardino et al. |
| 6,113,609 | A | 9/2000 | Adams |
| 6,117,159 | A | 9/2000 | Huebsch et al. |
| 6,126,686 | A | 10/2000 | Badylak et al. |
| 6,132,438 | A | 10/2000 | Fleischman et al. |
| 6,143,037 | A | 11/2000 | Goldstein et al. |
| 6,152,144 | A | 11/2000 | Lesh et al. |
| 6,165,183 | A | 12/2000 | Kuehn et al. |
| 6,165,204 | A | 12/2000 | Levinson et al. |
| 6,168,588 | B1 | 1/2001 | Wilson |
| 6,171,329 | B1 | 1/2001 | Shaw et al. |
| 6,174,322 | B1 | 1/2001 | Schneidt et al. |
| 6,174,330 | B1 | 1/2001 | Stinson |
| 6,183,443 | B1 | 2/2001 | Kratoska et al. |
| 6,187,039 | B1 | 2/2001 | Hiles et al. |
| 6,190,353 | B1 | 2/2001 | Makower et al. |
| 6,190,357 | B1 | 2/2001 | Ferrari et al. |
| 6,197,016 | B1 | 3/2001 | Fourkas et al. |
| 6,199,262 | B1 | 3/2001 | Martin |
| 6,206,895 | B1 | 3/2001 | Levinson |
| 6,206,907 | B1 | 3/2001 | Marino et al. |
| 6,214,029 | B1 | 4/2001 | Thill et al. |
| 6,217,590 | B1 | 4/2001 | Levinson |
| 6,221,092 | B1 | 4/2001 | Koike et al. |
| 6,227,139 | B1 | 5/2001 | Nguyen et al. |
| 6,228,097 | B1 | 5/2001 | Levinson et al. |

(56) References Cited

U.S. PATENT DOCUMENTS

| | | |
|---|---|---|
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint et al. |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,358,238 B1 | 3/2002 | Sherry |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,450,987 B1 | 9/2002 | Kramer |
| 6,460,749 B1 | 10/2002 | Levinson et al. |
| 6,482,224 B1 | 11/2002 | Michler et al. |
| 6,488,706 B1 | 12/2002 | Solymar et al. |
| 6,494,846 B1 | 12/2002 | Margolis |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,554,842 B2 | 4/2003 | Heuser et al. |
| 6,585,719 B2 | 7/2003 | Wang |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,790,173 B2 | 9/2004 | Saadat et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,867,249 B2 | 3/2005 | Lee et al. |
| 6,921,410 B2 | 7/2005 | Porter |
| 6,936,058 B2 | 8/2005 | Forde et al. |
| 6,984,203 B2 * | 1/2006 | Tartaglia et al. .............. 600/114 |
| 7,022,102 B2 | 4/2006 | Paskar |
| 7,469,722 B2 * | 12/2008 | Berland ........................ 138/155 |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 * | 12/2002 | Gainor et al. .................. 606/213 |
| 2003/0004533 A1 | 1/2003 | Dieck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0120337 A1 | 6/2003 | Van Tassel et al. |
| 2003/0139819 A1 | 7/2003 | Beer et al. |
| 2003/0171774 A1 | 9/2003 | Freudenthal et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0073242 A1 | 4/2004 | Chanduszko |
| 2004/0087968 A1 | 5/2004 | Core |
| 2004/0122360 A1 * | 6/2004 | Waldhauser et al. ...... 604/95.04 |
| 2004/0133236 A1 | 7/2004 | Chanduszko |
| 2004/0158124 A1 | 8/2004 | Okada |
| 2004/0176799 A1 | 9/2004 | Chanduszko et al. |
| 2004/0210301 A1 | 10/2004 | Obermiller |
| 2004/0234567 A1 | 11/2004 | Dawson |
| 2004/0249367 A1 | 12/2004 | Saadat et al. |
| 2005/0025809 A1 | 2/2005 | Hasirci et al. |
| 2005/0043759 A1 | 2/2005 | Chanduszko |

(56) References Cited

U.S. PATENT DOCUMENTS

| | | | |
|---|---|---|---|
| 2005/0080430 | A1 | 4/2005 | Wright et al. |
| 2005/0113868 | A1 | 5/2005 | Devellian |
| 2005/0131341 | A1 | 6/2005 | McGuckin et al. |
| 2005/0267523 | A1 | 12/2005 | Devellian et al. |
| 2005/0273135 | A1 | 12/2005 | Chanduszko et al. |
| 2005/0288786 | A1 | 12/2005 | Chanduszko |
| 2006/0122647 | A1 | 6/2006 | Callaghan et al. |
| 2006/0265004 | A1 | 11/2006 | Callaghan et al. |
| 2006/0271089 | A1 | 11/2006 | Alejandro et al. |
| 2007/0010851 | A1 | 1/2007 | Chanduszko et al. |
| 2007/0167981 | A1 | 7/2007 | Opolski |

FOREIGN PATENT DOCUMENTS

| | | | |
|---|---|---|---|
| EP | 0474887 | A1 | 3/1992 |
| EP | 0 839 549 | | 5/1998 |
| EP | 0 861 632 | | 9/1998 |
| EP | 1013227 | A2 | 6/2000 |
| EP | 1046375 | A1 | 10/2000 |
| EP | 1222897 | A2 | 7/2002 |
| WO | WO-96/25179 | A1 | 8/1996 |
| WO | WO-96/31157 | A1 | 10/1996 |
| WO | WO-98/07375 | A1 | 2/1998 |
| WO | WO-98/08462 | | 3/1998 |
| WO | WO-98/16174 | | 4/1998 |
| WO | WO-98/29026 | A2 | 7/1998 |
| WO | WO-98/51812 | | 11/1998 |
| WO | WO-99/05977 | A1 | 2/1999 |
| WO | WO-98/18864 | | 4/1999 |
| WO | WO-99/18862 | A1 | 4/1999 |
| WO | WO-99/18864 | | 4/1999 |
| WO | WO-99/18870 | A1 | 4/1999 |
| WO | WO-99/18871 | A1 | 4/1999 |
| WO | WO-99/30640 | A1 | 6/1999 |
| WO | WO-99/66846 | | 12/1999 |
| WO | WO-00/27292 | A1 | 5/2000 |
| WO | WO-00/44428 | A2 | 8/2000 |
| WO | WO-01/08600 | | 2/2001 |
| WO | WO-01/19256 | | 3/2001 |
| WO | WO-01/21247 | A1 | 3/2001 |
| WO | WO-01/28432 | | 4/2001 |
| WO | WO-01/30268 | A1 | 5/2001 |
| WO | WO-01/49185 | A1 | 7/2001 |
| WO | WO-01/78596 | A1 | 10/2001 |
| WO | WO-01/93783 | | 12/2001 |
| WO | WO-02/17809 | A1 | 3/2002 |
| WO | WO-02/24106 | A3 | 3/2002 |
| WO | WO-03/024337 | A1 | 3/2003 |
| WO | WO-03/053493 | A1 | 7/2003 |
| WO | WO-03/059152 | | 7/2003 |
| WO | WO 03/063732 | A | 8/2003 |
| WO | WO-03/077733 | A2 | 9/2003 |
| WO | WO-03/082076 | | 10/2003 |
| WO | WO-03/103476 | A2 | 12/2003 |
| WO | WO-2004/032993 | | 4/2004 |
| WO | WO-2004/037333 | | 5/2004 |
| WO | WO-2004/043266 | | 5/2004 |
| WO | WO-2004/043508 | | 5/2004 |
| WO | WO-2004/052213 | | 6/2004 |
| WO | WO-2005/006990 | | 1/2005 |
| WO | WO-2005/018728 | | 3/2005 |
| WO | WO-2005/027752 | | 3/2005 |
| WO | WO-2005/074813 | | 8/2005 |
| WO | WO-2005/092203 | | 10/2005 |
| WO | WO-2005/110240 | | 11/2005 |
| WO | WO-2005/112779 | | 12/2005 |
| WO | WO-2006/036837 | | 4/2006 |
| WO | WO-2006/102213 | | 9/2006 |

OTHER PUBLICATIONS

Bachthaler, M. et al., "Corrosion of Tungsten Coils After Peripheral Vascular Embolization Theraphy: Influence on Outcome and Tungsten Load", Catherization and Cardiovascular Interventions, vol. 62, pp. 380-384, 2004.

European Examination Report, European Application No. 03729663.9, mailed Jul. 16, 2008 (5 Pages).
European Examination Report, European Application No. 03731562.9, mailed Jul. 18, 2008 (3 Pages).
European Examination Report, European Application No. 03779297.5, mailed arch 15, 2007 (6 Pages).
European Examination Report, European Application No. 04781644.2, mailed Aug. 23, 2007 (3 Pages).
European Search Report, European Application No. 03729663.9, mailed Feb. 20, 2008 (3 Pages).
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1), pp. 185-192.
International Search Report and Written Opinion, International Patent Application No. PCT/US06/41255, mailed Jun. 13, 2008 (6 pgs).
Meier, MD, Bernhard, et al., "Contemporary Management of Patent Foramen Ovale," American Heart Association, Inc., Circulation, 2003, vol. 107, pp. 5-9.
Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.
Ramanathan, G., et. al., "Experimental and Computational Methods for Shape Memory Alloys," 15th ASCE Engineering Mechanics Conference, Jun. 2-5, 2002.
Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.
Ruiz, et al., "The Puncture Technique: A New Method for Transcatheter Closure of Patent Foramen Ovale," Catheterization and Cardiovascular Interventions, 2001, vol. 53, pp. 369-372.
Shabalovskaya, S., "Surface Corrosion and Biocompatibility Aspects of Nitinol as and Implant Material," Bio-Medical Materials and Engineering, 2002, vol. 12, pp. 69-109.
SMST-2000, "Proceedings of the International Conference on Shape Memory and Superelastic Technologies," Apr. 30-May 4, 2000, Asilomar Conference Center.
Stockel, "Nitinol Medical Devices and Implants," SMST-2000 Conference Proceedings, 2001, pp. 531-541.
Uchil, J., "Shape Memory Alloys—Characterization Techniques," Pramana—Journal of Physics, 2002 vol. 58 (5)(6), pp. 1131-1139.
Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.
International Search Report and Written Opinion, International Patent Application No. PCT/US08/59429, mailed Sep. 5, 2008 (9 pgs).
International Search Report and Written Opinion, International Patent Application No. PCT/US08/59448, mailed Sep. 5, 2008 (8 pages).
International Search Report and Written Opinion, International Patent Application No. PCT/US08/60738, mailed Sep. 3, 2008 (10 pages).
International Search Report for International Patent Application No. PCT/AU03/00759, filed Jun. 19, 2003.
International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs).
International Search Report, International Application No. PCT/US03/17390 mailed Oct. 6, 2003 (4 pgs).
International Search Report, International Application No. PCT/US03/17715, mailed Mar. 24, 2004 (2 pgs).
International Search Report, International Application No. PCT/US03/32133, mailed Apr. 22, 2004 (1 pg).

(56) References Cited

OTHER PUBLICATIONS

International Search Report, International Application No. PCT/US03/34003 mailed Oct. 3, 2004 (4 pgs).
International Search Report, International Application No. PCT/US03/35479, mailed Apr. 14, 2004 (2 pages).
International Search Report, International Application No. PCT/US03/35998 mailed Jun. 16, 2004 (5 pgs).
International Search Report, International Application No. PCT/US03/39253, mailed Apr. 19, 2004 (4 pgs).
International Search Report, International Application No. PCT/US04/022643, mailed Mar. 31, 2005 (2 pgs).
International Search Report, International Application No. PCT/US04/026998, mailed Apr. 22, 2005 (5 pgs).
International Search Report, International Application No. PCT/US04/029978, mailed Jan. 26, 2005 (3 pgs).
International Search Report, International Application No. PCT/US05/006703, mailed Jul. 25, 2005 (3 pgs).
International Search Report, International Application No. PCT/US05/013705 mailed Aug. 4, 2005 (4 pgs).
International Search Report, International Application No. PCT/US05/015382, mailed Oct. 6, 2005 (4 pgs).
International Search Report, International Application No. PCT/US05/34276, mailed Oct. 9, 2007.
International Search Report, International Application No. PCT/US06/009978, mailed Jul. 13, 2006 (2 pgs).
International Search Report, International Application No. PCT/US07/065546, mailed Oct. 29, 2007. 4 pages.
International Search Report, International Application No. PCT/US2007/065526, mailed Aug. 8, 2007 (5 pgs).
International Search Report, International Application No. PCT/US2007/065541, mailed Aug. 7, 2007 (4 pgs).
International Search Report, International Application No. PCT/US97/14822, mailed Feb. 20, 1998 (2 pgs).
International Search Report, International Application No. PCT/US97/17927, mailed Feb. 10, 1998 (1 pg).
Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.
Kimura, A., et al., "Effects of Neutron Irradiation on the Transformation Behavior in Ti-Ni Alloys," Abstract, Proceedings of the Int'l Conf. on Marienstic Transformations, 1992, pp. 935-940.
Klima, U., "Magnetic Vascular Port in Minimally Invasive Direct Coronary Artery Bypass Grafting," Circulation, 2004, II-55-II-60.

* cited by examiner

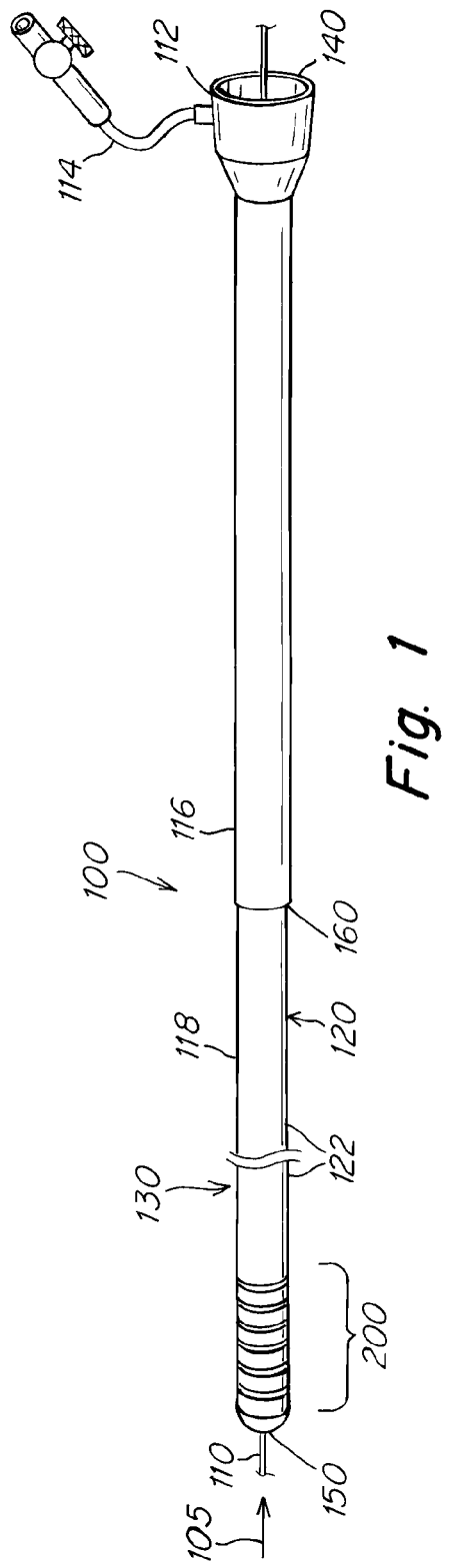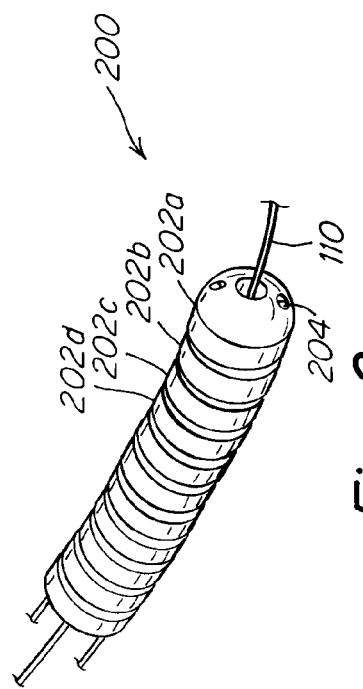

FLEXIBLE CATHETER SYSTEM

CROSS-REFERENCE TO RELATED APPLICATIONS

This application claims under 35 U.S.C. §119(e) priority to and the benefit from U.S. Provisional Patent Application No. 60/923,985, filed on Apr. 18, 2007, entitled "Flexible Catheter System", the disclosure of which is incorporated in its entirety by reference herein.

BACKGROUND OF THE INVENTION

1. Field of the Invention

The invention relates to catheter systems for delivery and/or retrieval of medical devices.

2. Description of Related Art

In many minimally invasive medical procedures, an introducer sheath or catheter is inserted in a blood vessel to gain access to a site within a patient's body for a diagnostic or therapeutic procedure, and used to deliver medical devices, including medical implants. Medical technology has produced a number of medical devices which are designed to be compressed into a first configuration, such as through a small diameter tube or catheter, in order to facilitate introduction through the vascular system, and to subsequently expand into an expanded configuration at a desired site in the body. For example, such devices can be intended to occlude defects or holes in the heart, such as intracardiac occluders, or to contact the walls of a passageway or blood vessel, in the case of vena cava filter or stents.

Among these devices, intracardiac occluders present special challenges for a delivery system. First, the occluder must be very carefully and precisely deployed at the treatment site to assure proper closure. Second, the tortuous anatomy of the cardiovascular system necessitates a delivery system capable of traversing the small radii of curvature of the vasculature and the confines of the heart chamber for delivery of the occluder to the deployment site.

Numerous systems for percutaneous catheter delivery of medical devices have been devised over the years in order to assist physicians in delivering and positioning medical devices within the human body in a minimally invasive manner. A common problem with many of these percutaneous delivery systems is that they can often adversely and unpredictably affect the position of the device upon deployment. For example, the released position of a medical implant may be different from its final position while still attached to the delivery system. In such case, the physician is forced to estimate the effect of this difference, compensate for this effect in positioning the implant, and take such effect into consideration when assessing final implant position prior to its release. Additionally, the movement of the implant that occurs following release from its delivery system can be unpredictable. Thus, the resulting improper positioning of such an implant can lead to unfavorable outcomes, such as a residual leak in the case of intracardiac occluders, or, in some extreme case, embolization of the implant.

BRIEF SUMMARY OF THE INVENTION

In one embodiment, the invention provides a conduit for insertion into a living body includes a plurality of adjacent segments. Each of the plurality of segments have a front face, a back face, and a central axis. The front faces of the segments are adjacent to the back faces of adjacent segments and form a flexible joint between the adjacent segments and enable the segments to be deflected from a configuration wherein the central axes of the segments are aligned. The conduit also includes a main lumen defined by the plurality of adjacent segments. The main lumen passes through the front and back faces of the segments. The conduit further includes a first side lumen defined by the plurality of adjacent segments. The first side lumen is disposed within the segments at a location radially distant from the central axes of the segments. The conduit includes a first wire disposed in the first side lumen. The first wire is joined to a most distal segment of the plurality of segments. The first wire is for selectively applying a force to the most distal segment to cause the plurality of segments to be deflected from a configuration wherein the central axes of the segments are aligned.

In some embodiments, the conduit includes a second side lumen defined by the plurality of adjacent segments. The second side lumen is disposed within the segments at a location radially distant from the central axes of the segments. The first wire can be disposed in the second side lumen. The first side lumen can be disposed across the central axis from the second side lumen.

In certain embodiments, the conduit includes a second wire disposed in the second side lumen. The second wire is joined to the most distal segment of the plurality of segments. The second wire is for selectively applying a force to the most distal segment to cause the plurality of segments to be deflected from a configuration wherein the central axes of the segments are aligned.

In various embodiments, the conduit includes a relatively rigid catheter section attached to the most proximal segment of the plurality of segments.

In some embodiments, the conduit can include one or more snare lumens defined by the plurality of adjacent segments. The snare lumens are disposed within the segments at a location radially distant from the central axes of the segments. One or more snare wires can be disposed in snare lumens. The snare wires are for releasably attaching to an implant device.

In other embodiments, a method includes introducing a conduit, as described herein, into a vasculature of a living body, and selectively applying a force to at least one wire disposed in a side lumen of the conduit to direct a distal end of the conduit to a desired site within the vasculature of the living body.

In various embodiments, the method above can also include withdrawing a deployed implant device into an inner lumen of a sheath through which the conduit passes, and withdrawing the conduit from the vasculature of a living body.

In certain embodiments, a method includes forming a conduit for insertion into a vasculature of a living body. The conduit includes a plurality of adjacent segments. Each of the plurality of segments has a front face, a back face, and a central axis. The front faces of the segments are adjacent to the back faces of adjacent segments and form a flexible joint between the adjacent segments and enable the segments to be deflected from a configuration wherein the central axes of the segments are aligned. The conduit also includes a main lumen defined by the plurality of adjacent segments. The main lumen passes through the front and back faces of the segments. The conduit further includes a first side lumen defined by the plurality of adjacent segments. The first side lumen is disposed within the segments at a location radially distant from the central axes of the segments. The method also includes disposing a first wire in the first side lumen. The first wire is joined to a most distal segment of the plurality of segments. The first wire is for selectively applying a force to the most distal segment to cause the plurality of segments to be deflected from a configuration wherein the central axes of the segments are aligned.

The forgoing and other features and advantages will become apparent from the following drawings, detailed description, and claims.

BRIEF DESCRIPTION OF THE DRAWINGS

FIG. 1 is a schematic illustration of a delivery system according to an embodiment of the invention;

FIG. 2 is a detail view of a distal portion of a delivery system according to an embodiment of the invention;

DETAILED DESCRIPTION

Figure 3A:
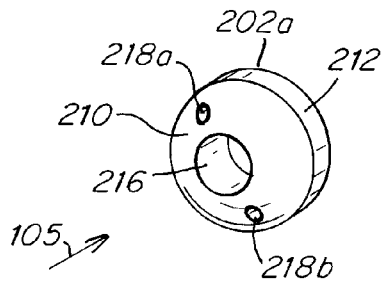
FIG. 3A is a detail view of a front side of a disk element of a distal portion of a delivery system when viewed from the direction 105 of FIG. 1 according to an embodiment of the invention.

Embodiments of the invention are directed to aspects of a catheter system for delivering, and optionally, retrieving, medical devices within the body through the vasculature (e.g., medical implants, drug release devices, diagnostic devices, etc.). Embodiments of the invention have particular utility for delivering, or retrieving, medical implants in the heart. Embodiments of the invention may be used, for example, to deliver septal occluders used to occlude anatomical apertures, such as atrial septal defects (ASD), ventricular septal defects (VSD) or patent foramen ovale (PFO). In this application, "distal" refers to the direction away from a sheath insertion location and "proximal" refers to the direction nearer the insertion location.

Referring to the drawings, wherein like reference numerals designate identical or corresponding parts throughout several views, and specifically to FIG. 1, a delivery system 100 is illustrated, including a sheath 116, having a lumen extending from one end to the other, and a catheter 118 slidably disposed within the lumen of the sheath 116. The sheath 116 has been retracted proximally to reveal a portion of the catheter 118. The catheter 118 has a proximal portion 120 and a distal portion 130. The catheter 118 includes a central lumen extending from one end to the other. The catheter 118 includes a main catheter portion 122 and a flexible portion 200 connected to the main catheter portion 122. The flexible portion 200 is relatively flexible as compared to the main catheter portion 122 which is relatively rigid. In the embodiments described herein, the sheath 116 may also be described as a catheter, thus, the terms can be used interchangeably. Similarly, the terms "delivery system" and "catheter system" can be used interchangeably.

The delivery system 100 further includes a hub portion 112 and a side port 114. A medical instrument or implantable device to be inserted into a patient is placed through a proximal end 140 of the delivery system 100 and exits the sheath 116 at a distal end 160 of the sheath. In certain embodiments, the delivery system 100 further includes a delivery wire 110 slidably disposed within the lumen of the catheter 118. As described in more detail below, the delivery wire 110 can be attached to a portion of a medical device, such as a medical implant, and can be used to deploy the medical implant to a desired location within the body. However, the delivery wire 110 is not required, and is omitted in certain other embodiments.

FIG. 2 shows the flexible portion 200 of the catheter 118. As shown in FIG. 2, flexible portion 200 is made up of a plurality of segments. In the embodiment shown, the segments are in the form of disk elements, such as disk elements 202a, 202b, 202c, and 202d, collectively referred to as "disk elements 202", linked in series. Although the disk elements 202 are separate, the disk elements 202 are connected by one or more connecting wires 204, described in greater detail below. Because the multiple disk elements 202 are separate from each other, the flexible portion 200 exhibits a lower degree of stiffness than if it were constructed of a solid piece of material. Thus, as explained in greater detail below, certain undesirable forces that might otherwise be imparted by a relative stiff catheter portion can be avoided during the deployment of a medical device.

Although only the distal portion 130 of the catheter includes the flexible portion 200 in the illustrated embodiment, in various embodiments, a longer or shorter flexible portion 200 with disk elements 202 can be incorporated in the catheter 118. In some embodiments, main catheter portion 122 may accordingly be relatively short while the flexible portion 200 is relatively long. In other embodiments, the entire length of the catheter 118 is comprised of flexible portion 200, which includes disk elements 202. The flexible portion 200 of the catheter 118 that includes disk elements 202 will exhibit a relatively high degree of flexibility, specifically compared with any portions that are formed by main catheter portion 122. In one embodiment, the sheath 116 covers the entire length of the catheter 118 including its distal portion 130 and its proximal portion 120, or main catheter portion 122 and the flexible portion 200. In another embodiment, as the sheath 116 is retracted proximally, the distal portion 130 of the catheter 118 is exposed, including a portion of or the entirety of flexible portion 200 of the catheter 118.

Figure 3B:
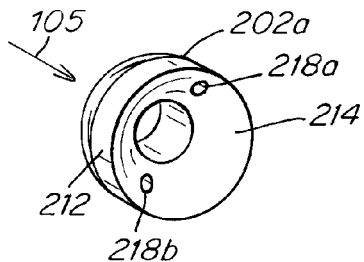
FIG. 3B is a detail view of a back side of a disk element of a distal portion of a delivery system when viewed from the direction 105 of FIG. 1 according to an embodiment of the invention.

FIGS. 3A and 3B illustrate detailed views of two sides of a single disk element 202a. Disk element 202a has a circular outer perimeter. Disk element 202a has a front face 210, a side wall 212 and a back face 214. The front face 210 has a ball-shape, i.e., is convex, and the back face 214 has a socket shape, i.e., is concave. The front face 210 and the back face 214 are designed to fit one within the other so that identical disk elements 202 can be fitted together end-to-end with a ball of one disk element 202 fitting into a socket of another, thereby forming a joint. Optionally, the front and back faces of adjacent disk elements 202 are connected. This connection can be a mechanical connection, for example, a flexible member joining the disk elements 202. The connection can also be a magnetic connection. Other types of connections can exist between the disk elements 202, so long as the flexibility of the flexible portion 200 is maintained. In other words, the front face 210 of one disk element 202 and back face 214 of another disk element 202 cooperate to enable the disks elements to change their alignment relative to each other.

In some embodiments, the front face 210 of one disk element 202 has a profile that fits flush against the back face 214 of another disk element. In such an embodiment, no gap is maintained between the nesting surfaces of the front and back faces of the adjacent disk elements 202. Although a gap is shown between disk elements 202 in FIGS. 1, 2, 4, 5A, and 5C-5E, it is understood that this is for the purpose of illustrating that disk elements 202 are separate. It is understood that a gap may or may not exist between disk elements 202. Therefore, in other embodiments, a gap is maintained between a portion of the nesting surfaces of the front and back faces of the adjacent disk elements 202. For example, the radius of curvature of the front face 210 can be smaller than that of the back face 214 of adjacent disk elements 202.

The disk element 202a further includes a central lumen 216, that extends along a longitudinal axis, from the front face 210 to the back face 214. The central lumen 216 is of sufficient size to allow the delivery wire 110, to be slidably disposed therein. During delivery of a medical device, such as a medical implant, the delivery wire 110 is attached to a portion of the medical implant and is used to deploy the implant. In such embodiments, the delivery wire enters the back face 214 of each of the disk elements 202 and exits the front face 210 of each of the disk elements 202. Thus, the delivery wire 110 passes into the proximal end 140 of the delivery system and eventually through the flexible portion 200 of the catheter 118 for attachment to the implant. The central lumen 216 may also be sized sufficiently to allow other mechanisms to facilitate delivery of a medical device to be slidably disposed therein.

The disk element 202a further includes two secondary lumens 218a and 218b, that extend from the front face 210 to the back face 214, and parallel to, but offset from, the center longitudinal axis and from central lumen 216. The secondary lumens 218a and 218b are preferably evenly distributed around the periphery of disk element 202a and at an equal radial distance from the axis. The secondary lumens 218a and 218b allow connecting wire(s) 204 to be slidably disposed therethrough. The inner diameter of the secondary lumens 218a and 218b is selected to provide sufficient space to allow connecting wire(s) 204 to slide within the lumens.

The disk element 202 is constructed of material with sufficient strength to maintain open central lumen 216 and secondary lumens 218a and 218b. The material is also sufficiently lubricious, or is treated to be sufficient lubricious, to allow the nested surfaces of disk elements 202 to move relative to each other. Likewise, the material provides for low friction between the inside surface of secondary lumens 218a and 218b and connecting wire(s) 204 disposed therethrough. Non-limiting examples of suitable materials include moldable plastics and metals.

The connecting wire 204 can be a wire-like or thread-like element and can be made of any suitable material and, in some embodiments, is a suture. In various embodiments, the wires can be made of a variety of materials and the term "wire" encompasses filaments, threads, sutures, single or multiple-strand wires, etc. An illustrative example includes suture wire with a diameter of 0.005 inches. The even distribution of secondary lumens 218a and 218b allows for a balanced application of forces to control the direction of the distal portion 130 of the catheter 118.

Although two secondary lumens 218a and 218b are shown in FIGS. 3A and 3B, some embodiments include additional or fewer secondary lumens. For example, some embodiments include three, four, five or more secondary lumens. In some embodiments, all secondary lumens run parallel to the central lumen 216 and are evenly distributed around the central lumen 216. In other embodiments, the secondary lumens are not evenly distributed around the central lumen 216. The function of the secondary lumens 218a and 218b and the connecting wire(s) 204 is described below.

Figure 4:
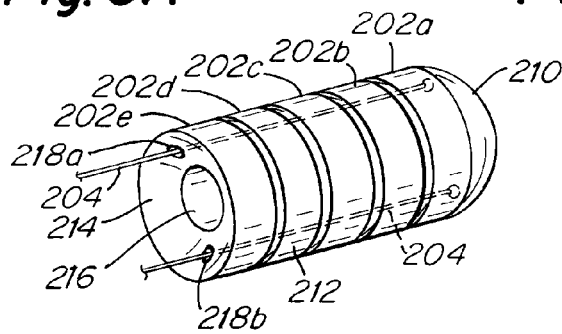
FIG. 4 is a detail view of disk elements of a distal portion of a delivery system according to an embodiment of the invention.

As discussed with respect to FIG. 2, and also illustrated in FIG. 4, multiple disk elements 202 similar to disk element 202a are connected end-to-end to form the flexible portion 200 of the catheter 118. The front face 210 of a first disk element 202a is disposed at the distal end 150 of the catheter 118. The back face 214 of the first disk element 202a is positioned adjacent to a front face 210 of a second disk element 202b. The front face 210 of disk element 202b fits within the back face 214 of the first disk element 202a in a ball-and-socket configuration.

The central lumens 216 of disk element 202a and 202b are adjoining, forming an extended central lumen, i.e., the central lumen of catheter 118. Similarly, the secondary lumens 218a and 218b are also adjoining, forming extended secondary lumens. The disk elements 202 are interconnected by connecting wire(s) 204, such as suture(s), which extend through secondary lumens 218a and 218b from one end of the flexible portion 200, comprising the disk elements 202, to the other end.

According to some embodiments, the distal end of the connecting wire(s) 204 is connected to the most distal of the disk elements 202, e.g., disk element 202a of FIG. 2. Meanwhile, the proximal end of the connecting wire(s) 204 can be manipulated by a clinician through a control mechanism at the central hub 112. As described above, some embodiments of delivery system 100 have both the flexible portion 200 and the relatively rigid main catheter portion 122. In such embodiments, lumens that correspond to secondary lumens 218a and 218b are provided through the relatively rigid main catheter portion 122. Thus, the connecting wire(s) 204 pass from the central hub 112 through the corresponding lumens in the relatively rigid catheter portion 122 to the secondary lumens 218a and 218b. In preferred embodiments, a single continuous connecting wire extends from the central hub 112, through one secondary lumen to the distal end 150, and returns to the central hub 112 through the other secondary lumen.

As all connecting wires 204 are tightened, i.e. pulled proximally, the joints between the disk elements 202 are tightened, and the catheter 118 exhibits a great degree of stiffness at its flexible portion 200. As all connecting wires 204 are loosened, the joints between the disk elements 202 are loosened, and the catheter 118 presents a great degree of flexibility at its flexible portion 200. In addition, connecting wires 204 can also be selectively loosened and tightened individually. When one connecting wire 204 is tightened and others remain loose, the adjoining ball-and-socket faces 210 and 214 of the connecting elements 202 are able to move with respect to each other. As a result, the distal portion 130 of the catheter 118 bends in the direction of the tightened connecting wire 204. Similarly, as two or more connecting wires 204 are tightened and others remain loose, the catheter 118 responds accordingly. Further still, some connecting wires 204 can be selectively loosened to cause the flexible portion 200 to deflect in the direction opposite to the loosened connecting wire(s) 204. One advantage of the embodiments of the flexible portion 200 is that the flexibility allows the implant to assume its natural deployment position while remaining attached to the delivery system 100.

Operation of the delivery system 100 and, specifically catheter 118, will now be described. For implant delivery, a medical implant can be secured at the distal end of the catheter 118. During delivery, as the catheter 118 travels through the lumen of the sheath 116, the direction of the catheter 118 can be manipulated by tightening one or more connecting wires 204, e.g., by pulling the connecting wire(s) 204 proximally.

In yet further embodiments, flexible portion 200 has a single secondary lumen 218a, through which a single connecting wire 204 passes. In such an embodiment, as the connecting wire 204 is tightened, the disk elements 202 of flexible portion are deflected away from a straight configuration.

As described above, the secondary lumens 218a and 218b (and other secondary lumens, if provided) are of sufficient inner diameter to allow connecting wires 204 to slide within the lumen and steer the disk elements 202. An illustrative example of flexible portion 200 includes disk elements 202 having secondary lumens with an inner diameter of 0.020 inches for use with 0.005 inch diameter suture wire serving as connecting wire(s) 204. In some embodiments, the secondary lumens have a circular cross-section. However, secondary lumens 218a and 218b can have any cross-sectional shape, e.g., square, rectangular, or oval, as long as connecting wires 204 are permitted to slide within the secondary lumens 218a and 218b.

In certain embodiments, during delivery, a medical device is secured to the distal end 150 of catheter 118. Various medical devices require various attachment mechanisms between the device and the catheter, depending on the structure of the device, the technique required for delivering and deploying the device, and combinations thereof. In particular, some devices can be connected with a double attachment system, i.e., two connections between the device and the delivery system. For example, a single attachment can be provided between the device and the flexible portion 200 of catheter 118 to secure the device to the flexible portion. In addition, a second attachment is made between the device and the delivery wire 110, which is slidably disposed within the central lumen of the catheter 118. This enables the delivery wire 110 to manipulate portions of the medical device as it remains attached to the distal end 150 of the catheter 118. Although not required, in certain delivery procedures, the delivery wire 110 is manipulated to deploy the medical device; the delivery wire 110 is disconnected from the medical device and withdrawn proximally; and then the medical device is released from the delivery system 100.

For a medical implant with a dual-attachment requirement, the distal end 150 of the catheter 118 is modified to attach to the implant. Such modifications have been disclosed in U.S. patent application Ser. No. 11/110,975, entitled Delivery Systems and Methods for PFO Closure Device with Two Anchors, filed Apr. 20, 2005; U.S. patent application Ser. No. 11/070,027, entitled Delivery/Recovery System for Clover Leaf Septal Occluder, filed Mar. 2, 2005; U.S. patent application Ser. No. 11/235,661, entitled Occluder Device Double Securement System for Delivery/Recovery of Such Occluder Device, filed Sep. 26, 2005; U.S. patent application Ser. No. 11/849,015, entitled Implant-Catheter Attachment Mechanism Using Snare and Method of Use, filed Sep. 28, 2006; U.S. patent application Ser. No. 11/904,545, entitled Implant-Catheter Attachment Mechanism Using Snare and Method of Use, filed Sep. 27, 2007; U.S. patent application Ser. No. 11/516,305, entitled Delivery Device for Implant with Dual Attachment Sites, filed Sep. 6, 2006; all incorporated by reference herein.

Figure 5A:
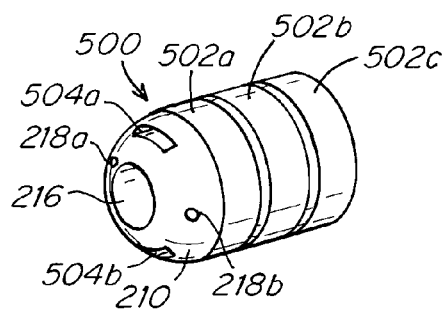
FIG. 5A is a detail view of a distal portion of a delivery system according to an embodiment of the invention.
Figure 5B:
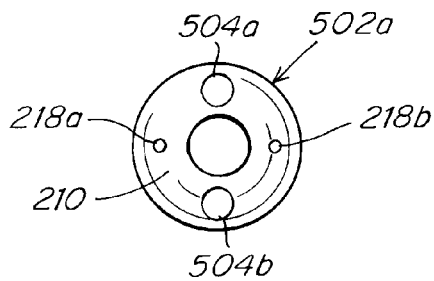
FIG. 5B is an end view of a distal portion of a delivery system according to an embodiment of the invention.
Figure 5C:
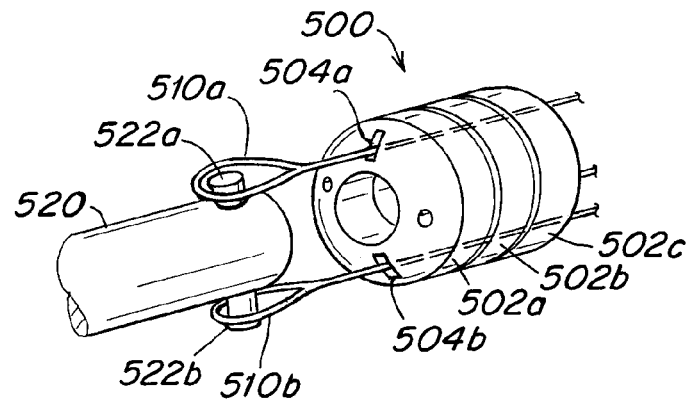
FIG. 5C is a detail view of a distal portion of a delivery system attached to an implant according to an embodiment of the invention.

FIGS. 5A-5C show an embodiment of the catheter described above incorporating a snare attachment disclosed in U.S. patent application Ser. No. 11/849,015 and U.S. patent application Ser. No. 11/904,545. As shown in those figures, the catheter 118 can be provided with a flexible catheter portion 500, similar to flexible portion 200. Catheter portion 500 is comprised of disk elements 502a, 502b and 502c, collectively referred to as disk elements 502, which are similar to disk elements 202. In addition to the central lumen 216 and secondary lumens 218a and 218b, additional snare lumens 504a and 504b are also provided as illustrated in FIGS. 5A and 5B. The snare lumens 504a and 504b permit a snare attachment mechanism between the device and the distal end of the catheter 118. In various embodiments, the snare attachment device can have different constructions, for example, with one or two loops.

FIG. 5C shows an embodiment with two looped snare wires 510a and 510b extending from secondary lumens 504a and 504b, respectively. This illustrative embodiment corresponds to the embodiment of the snare attachment mechanism shown in FIGS. 44A-44C of U.S. patent application Ser. No. 11/904,545. The looped ends of snare wires 510a and 510b provide snare attachment mechanisms between a medical implant 520 and the distal end of the catheter 118. The loop of snare wire 510a fits around a first projection 522a, which extends from a proximal end of the medical implant 520. Likewise, snare wire 510b fits around a second projection 522b.

As tension is maintained on snare wires 510a and 510b, the loops of the snare wires are constricted and engage their corresponding projections. Thus, the medical implant 520 is held snuggly against the front face of the disk element 502a. As tension is released from snare wires 510a and 510b, as shown in FIG. 5C, the looped ends of snare wires 510a and 510b open and release from projections 522a and 522b. In some embodiments, the snare wires 510a and 510b are biased so that upon being released from projections 522a and 522b, the snare wires deflect away from the projections to facilitate release of the medical implant 520. In such a case, the secondary lumens 504a and 504b can have a rectangular cross section with the longest side of the rectangle oriented radially away from the central axis of the catheter 118. In this way, the secondary lumens 504a and 504b permit the snare wires 510a and 510b to deflect away from the projections 522a and 522b.

Although not shown, in others embodiments, a single snare wire extends from secondary lumen 504a, curves around the first and second projections and reenters through lumen 504b, thereby forming a coil of wire around the proximal end of the medical implant 520. This wire can be extended and retracted at the distal end of the catheter 118. By extending the single wire, the coil of wire expands, thereby releasing the medical implant 520 (e.g., such as described in connection with the embodiment shown in FIG. 43 of U.S. patent application Ser. No. 11/904,545).

Figure 5D:
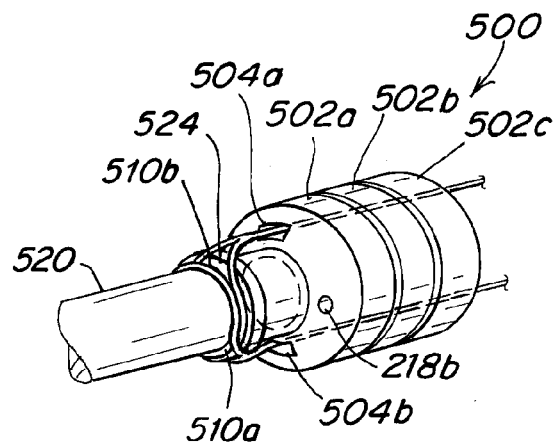
FIG. 5D is a detail view of a distal portion of a delivery system attached to an implant according to an additional embodiment of the invention.
Figure 5E:
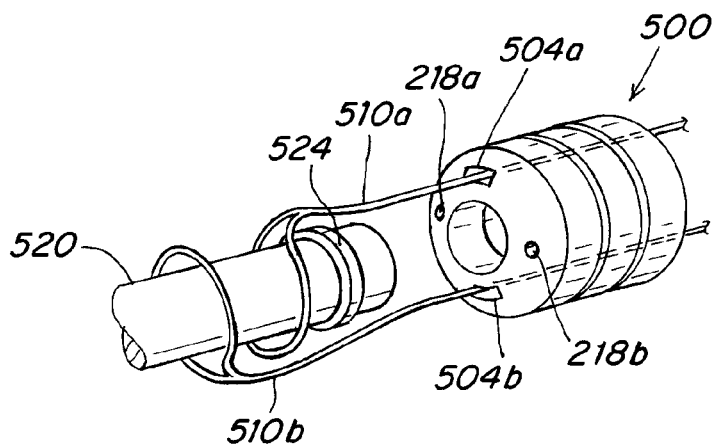
FIG. 5E is a detail view of a distal portion of a delivery system during the release of an implant according to an embodiment of the invention.

FIGS. 5D-5E shows another embodiment of the delivery system for use with the embodiment of the snare attachment mechanism shown in FIG. 45A of U.S. patent application Ser. No. 11/904,545. In this embodiment, the looped end of the first snare wire 510a extends from the first secondary lumen 504a and the second snare wire 510b extends from the second secondary lumen 504b. The loops of the snare wires 510a and 510b criss-cross over the proximal end of the medical implant 520 and are held in place by a flange 524. The first snare wire 510a passes through the first secondary lumen 504a, which is oriented at the top of the front face of disk element 502a, and the loop of the first snare wire 510a crosses over to snare the opposite side of the medical implant 520. The second snare wire 510b passes through the second secondary lumen 504b, which is oriented at the bottom of the front face of disk element 502a, and the loop of the second snare wire 510b crosses over to snare the opposite side of the medical implant 520. Thus, as tension is held on snare wires 510a and 510b, the loops in the snare wires are constricted, and the medical implant 520 is held in place against the distal end of flexible portion 500.

To release implant 520, snare wires 510a and 510b are pushed distally (or the catheter 118 is pulled proximally), to allow the loops in the snare wires 510a and 510b to expand and release from the proximal end of the medical implant 520. Various optional features to facilitate releasing the snare wires 510a and 510b from the medical implant 520 are described in U.S. patent application Ser. No. 11/904,545, and can be implemented in the embodiments described herein. Likewise, the other embodiments of the snare attachment mechanism disclosed in that application, and the other applications incorporated by reference, can be used with embodiments of the present invention. For example, the various single snare loop mechanisms illustrated in FIGS. 41-43 can be used with embodiments of the delivery system 100.

In the dual-snare wire embodiments described above, the snare wires can be released in sequence. Thus, one of the snare wires can be loosened while the other snare wire remains constricted. In such a case, the medical implant 520 remains at least partial secured to the distal end 150 of the catheter 118 (of the delivery system 100 shown in FIG. 1). Should the medical practitioner determine during the deployment of the medical implant 520 that the implant is not correctly positioned, the snare wire that remains constricted can be used to keep the medical implant 520 held snuggly against the distal end 150 of the catheter. Thus, the medical practitioner may withdraw the catheter 118 proximally into the sheath 116 with the medical implant 520 still attached. In some cases, this can enable the medical implant to collapse back into a reduced-profile configuration. In this way, the delivery system 100 may also be used to retrieve a medical device during the deployment procedure.

As mentioned above, the snare attachments described herein are illustrative examples of optional features of the distal end of flexible portion 500. Any of the modifications disclosed in the incorporated applications may be used with the embodiments described above. Similarly, other modifications are possible to allow for cooperation between the distal end of flexible portion 500 and a device to be implanted into a body. For example, a portion of the device to be implanted may have a concave surface that mates with the convex surface of the distal end of flexible portion 500. Likewise, the front face of the distal-most disk element 502a of flexible portion 500 can be modified to cooperate with the geometry of the device to be implanted.

The flexible delivery system 100 described herein has a wide variety of applications, and could be used to deliver, and optionally retrieve, various devices or implants to desired locations within the body.

The embodiments described herein have been provided by way of example and illustration only, and variations can be made therefrom without departing from the spirit and scope of the inventions described herein. For example, the embodiments described above have a central lumen extending through the center of the disk elements. However, it is within the scope of the invention to include two or more main lumens running in a side-by-side arrangement through the center of the catheter. Thus, while neither of the two or more main lumens is disposed in the true center of the disk elements or the catheter as a whole, it is understood that either or any of these main lumens can fulfill the role of and be described as a central lumen. Similarly, the embodiments described above have segments in the form of disk elements having circular cross-sections. The segments of the flexible portion of the catheter may have other cross-sectional geometries, such as oval, and remain within the scope of the invention.

The invention claimed is:

1. A conduit for insertion into a living body, the conduit comprising:
    a hub portion at a proximal end of the conduit;
    a plurality of adjacent segments, each of the plurality of segments having a front face, a back face, and a central axis, the front faces of the segments being adjacent to the back faces of adjacent segments for forming a flexible joint between the adjacent segments and for enabling the segments to be deflected from a configuration wherein the central axes of the segments are aligned;
    a main lumen defined by the plurality of adjacent segments, the main lumen passing through the front and back faces of the segments;
    a first side lumen defined by the plurality of adjacent segments, the first side lumen disposed within the segments at a location radially distant from the central axes of the segments;
    a first wire disposed in the first side lumen, the first wire being joined to a most distal segment of the plurality of segments, the first wire having a proximal end that can be manipulated through a control mechanism at the hub portion to selectively tighten the first wire and cause the most distal segment to bend in the direction of the tightened first wire;
    a first snare lumen defined by the plurality of adjacent segments, the first snare lumen disposed within the segments at a location radially distant from the central axes of the segments and a first snare wire disposed in the first snare lumen, the first snare wire having a looped end that extends from a distal end of the conduit for releasably attaching to an implant device, wherein the first snare wire is resiliently biased such that it automatically deflects the looped end away from the central axis of the most distal segment upon uncoupling of the looped end from the implant device; and
    a main catheter section attached to a most proximal segment of the plurality of segments.

2. The conduit of claim 1, further comprising a second side lumen defined by the plurality of adjacent segments, the second side lumen disposed within the segments at a location radially distant from the central axes of the segments.

3. The conduit of claim 2, the first wire further disposed in the second side lumen.

4. The conduit of claim 2, wherein the first side lumen is disposed across the central axis from the second side lumen.

5. The conduit of claim 2, further comprising a second wire disposed in the second side lumen, the second wire being joined to the most distal segment of the plurality of segments, the second wire having a proximal end that can be manipulated through the control mechanism to selectively tighten the second wire and cause the most distal segment to bend in the direction of the tightened second wire.

6. The conduit of claim 5, further comprising a third side lumen defined by the plurality of adjacent segments, the third side lumen disposed within the segments at a location radially distant from the central axes of the segments and a third wire disposed in the third side lumen, the third wire being joined at a first end of the third wire to the most distal segment of the plurality of segments, the third wire having a proximal end that can be manipulated through the control mechanism to selectively tighten the third wire and cause the most distal segment to bend in the direction of the tightened third wire.

7. The conduit of claim 6, wherein the side lumens are equally spaced from each other about the central axis.

8. The conduit of claim 1, wherein the segments are disk-shaped and the front face of at least some of the segments is convex and the back face of at least some of the segments is concave.

9. The conduit of claim 1, wherein the main lumen is disposed in the center of the plurality of segments.

10. The conduit of claim 1, further comprising a second snare lumen defined by the plurality of adjacent segments, the second snare lumen disposed within the segments at a location radially distant from the central axes of the segments and a second snare wire disposed in the second snare lumen, the second snare wire having a looped end that extends from a distal end of the conduit for releasably attaching to the implant device.

11. The conduit of claim 1, further comprising a distal-most segment, wherein a front face of the distal-most segment is shaped to facilitate attachment of the implant device to the distal-most segment.

12. A method comprising:
a) forming a conduit for insertion into a vasculature of a living body, the conduit comprising:
a hub portion at a proximal end of the conduit;
a plurality of adjacent segments, each of the plurality of segments having a front face, a back face, and a central axis, the front faces of the segments being adjacent to the back faces of adjacent segments for forming a flexible joint between the adjacent segments and for enabling the segments to be deflected from a configuration wherein the central axes of the segments are aligned;
a main lumen defined by the plurality of adjacent segments, the main lumen passing through the front and back faces of the segments;
a first side lumen defined by the plurality of adjacent segments, the first side lumen disposed within the segments at a location radially distant from the central axes of the segments;
a first snare lumen defined by the plurality of adjacent segments, the first snare lumen disposed within the segments at a location radially distant from the central axes of the segments and a first snare wire disposed in the first snare lumen, the first snare wire having a looped end that extends from a distal end of the conduit for releasably attaching to an implant device, wherein the first snare wire is resiliently biased such that it automatically deflects the looped end away from the central axis of the segments upon uncoupling of the looped end from the implant device; and
a main catheter section attached to a most proximal segment of the plurality of segments; and
b) disposing a first wire in the first side lumen, the first wire being joined to a most distal segment of the plurality of segments, the first wire having a proximal end that can be manipulated through a control mechanism at the hub portion to selectively tighten the first wire and cause the most distal segment to bend in the direction of the tightened first wire.

13. The method of claim 12, wherein the segments are disk-shaped and the front face of at least some of the segments is convex and the back face of at least some of the segments is concave.

14. The method of claim 12, further comprising forming a relatively rigid catheter section joined to the most proximal segment of the plurality of segments.

\* \* \* \* \*